United States Patent
Sugiyama et al.

(10) Patent No.: US 6,458,075 B1
(45) Date of Patent: Oct. 1, 2002

(54) ENDOSCOPIC FLEXIBLE TUBE

(75) Inventors: Akira Sugiyama, Kanagawa; Kikuo Iwasaka, Saitama; Masanao Abe, Saitama; Minoru Matsushita, Tokyo, all of (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/559,411

(22) Filed: Apr. 26, 2000

(30) Foreign Application Priority Data

Apr. 27, 1999 (JP) .............................. 11-119286

(51) Int. Cl.⁷ ................................................ A61B 1/00
(52) U.S. Cl. ...................................... 600/139; 600/140
(58) Field of Search ................................ 600/140, 139, 600/133, 143

(56) References Cited

U.S. PATENT DOCUMENTS

| | | | | |
|---|---|---|---|---|
| 4,753,222 A | * | 6/1988 | Morishita .................... | 600/140 |
| 4,899,787 A | * | 2/1990 | Ouchi et al. ................ | 138/131 |
| 4,944,287 A | | 7/1990 | Takahashi et al. | |
| 5,058,567 A | | 10/1991 | Takakashi et al. | |
| 5,217,002 A | * | 6/1993 | Katsurada et al. .......... | 600/139 |
| 5,394,864 A | | 3/1995 | Kobayashi et al. | |
| 5,448,988 A | * | 9/1995 | Watanabe .................... | 138/118 |
| 5,536,235 A | * | 7/1996 | Yabe et al. .................. | 138/118 |
| 5,788,714 A | | 8/1998 | Ouchi | |
| 5,873,866 A | * | 2/1999 | Kondo et al. ................ | 600/140 |
| 5,876,331 A | * | 3/1999 | Wu et al. .................... | 138/118 |
| 5,885,207 A | | 3/1999 | Iwasaka | |

FOREIGN PATENT DOCUMENTS

| | | |
|---|---|---|
| JP | 53157583 | 5/1977 |
| JP | 2-51601 | 11/1990 |
| JP | 3-42896 | 6/1991 |
| JP | 3-58725 | 9/1991 |
| JP | 5-95894 | 4/1993 |
| JP | 5-50287 | 7/1993 |
| JP | 5-50288 | 7/1993 |
| JP | 5-220102 | 8/1993 |
| JP | 5-277061 | 10/1993 |
| JP | 6-4058 | 1/1994 |
| JP | 8-136823 | 5/1996 |
| JP | 8-171059 | 7/1996 |
| JP | 9-51870 | 2/1997 |
| JP | 2641789 | 5/1997 |

* cited by examiner

Primary Examiner—Linda C. M. Dvorak
Assistant Examiner—Jocelyn Ram
(74) Attorney, Agent, or Firm—Greenblum & Bernstein, P.L.C.

(57) ABSTRACT

An endoscopic flexible tube that allows for easy fabrication of a jacket of a multi-layered structure that is adequately protected against separation of overlying layers. Two adjacent layers in the multi-layered structure portion of the jacket are integrally combined via an area that comprises a mixture of the constituent materials of the two layers.

6 Claims, 8 Drawing Sheets

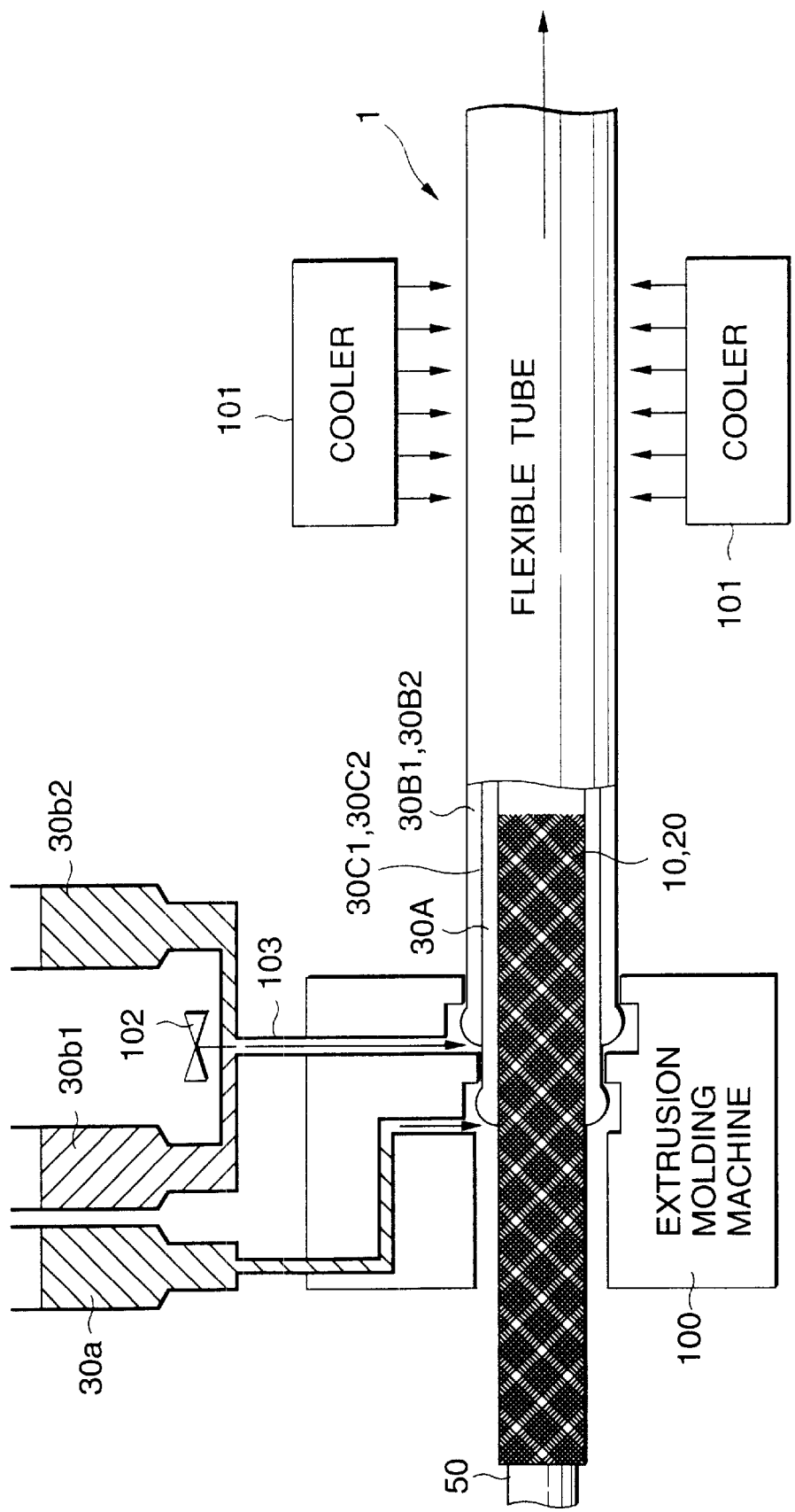

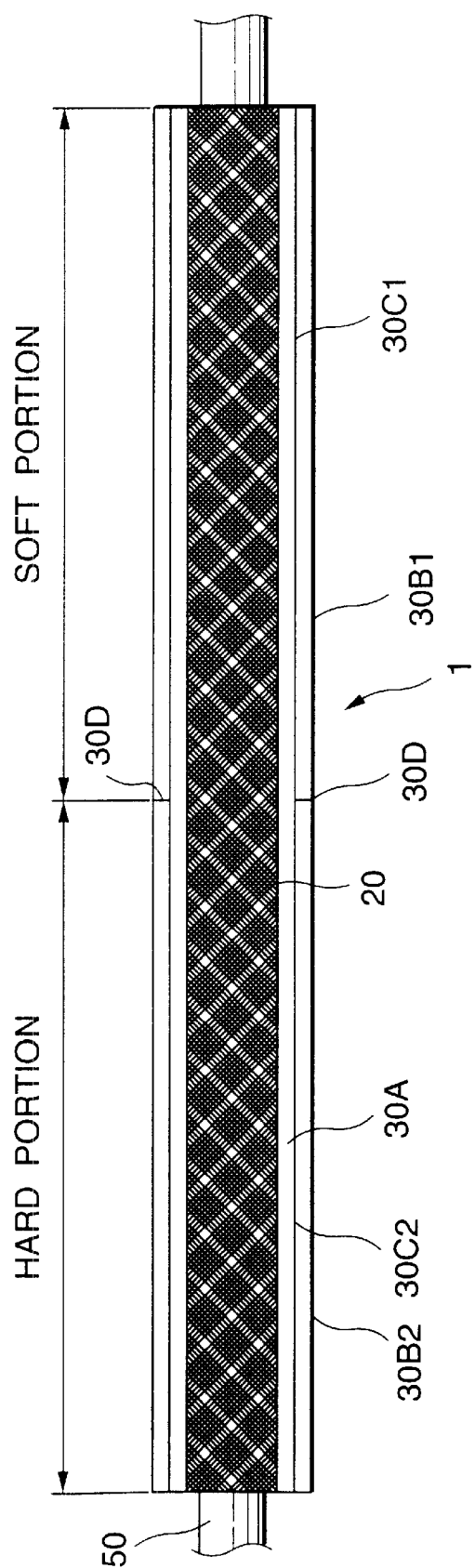

ENDOSCOPIC FLEXIBLE TUBE

BACKGROUND OF THE INVENTION

The present invention relates to an endoscopic flexible tube serving as a sheath for the insertion portion or other parts of an endoscope.

Endoscopic flexible tubes generally comprise a helical tube, a reticulate tube covering the outer surface of the helical tube, and a jacket covering the outer surface of the reticulate tube. The helical tube is formed of a metal or plastic strip wound spirally in a specified diameter. The reticulate tube is formed of braided thin metal wires. The jacket is made of a synthetic resin material.

The jacket commonly has a simple single-layered structure but it is by no means rare that a plurality of layers are superposed to provide a "multi-layered structure" that adds several improvements on the flexible tube such as greater ease with which it can be inserted into a body cavity and higher chemical resistance.

A problem with the jacket having a multi-layered structure is that the individual layers must be securely bonded to insure that they will not separate from each other even if the jacket is subjected to repeated bends during service.

This not only adds to the time and manpower required by the overall manufacturing process; due, for example, to uneven coating of adhesives, the adhesion between layers in the multi-layered structure portion may become locally insufficient or the adhesives may deteriorate with time to cause separation of adjacent layers.

SUMMARY OF THE INVENTION

An object, therefore, of the invention is to provide an endoscopic flexible tube that allows for easy fabrication of a jacket of a multi-layered structure that is adequately protected against separation of overlying layers.

According to the invention, two overlapping layers in a multi-layered structure portion of a jacket of an endoscopic flexible tube are integrally combined via an area that comprises a mixture of the constituent materials of said two layers. The constituent materials of said two layers are preferably mixed together in a molten state to form the mixture. Because of this structure, the jacket is resistant to separation between overlapping layers.

In a preferred embodiment, an endoscopic flexible tube comprises a helical tube formed of a strip wound in turns of a coil that are spaced by gaps in the pitch direction, a reticulate tube that is covered on the surface of said helical tube and which is formed of reticulately braided bundles of wires, and a flexible jacket that is coated on the outer surface of said reticulate tube and at least part of which has a multi-layered structure comprising a plurality of superposed layers, wherein two overlapping layers in the multi-layered structure portion of said jacket are integrally combined via an area that comprises a mixture of the constituent materials of said two layers.

If desired, the inner layer of the multi-layered structure portion of said jacket may be made of a soft synthetic resin material and the outer layer of a harder material having high chemical resistance.

In another embodiment, either the inner layer or the outer layer or both the inner and outer layers of the multi-layered structure portion of said jacket may have a plurality of portions with different characteristics along the longitudinal axis of said endoscopic flexible tube, with adjacent ones of said portions being integrally combined via an area that comprises a mixture of the constituent materials of said two adjacent portions.

The mixture area in the multi-layered structure portion of said jacket may be such that it was formed of the constituent materials on the opposite sides that intermingled when they were molten simultaneously. If desired, the inner layer of the multi-layered structure portion of said jacket may protrude inward of said reticulate tube through the mesh openings therein.

The present disclosure relates to the subject matter contained in Japanese patent application No. Hei. 11-119286 (filed on Apr. 27, 1999), which is expressly incorporated herein by reference in its entirety.

BRIEF DESCRIPTION OF THE DRAWINGS

In the accompanying drawings:

FIG. 7 is a sketch showing in longitudinal section how the endoscopic flexible tube according to the second embodiment of the invention can be fabricated; and FIG. 8 is a longitudinal section of the endoscopic flexible tube according to the second embodiment of the invention.

DESCRIPTION OF THE PREFERRED EMBODIMENT

Embodiments of the invention are described below with reference to the accompanying drawings.

Figure 4:
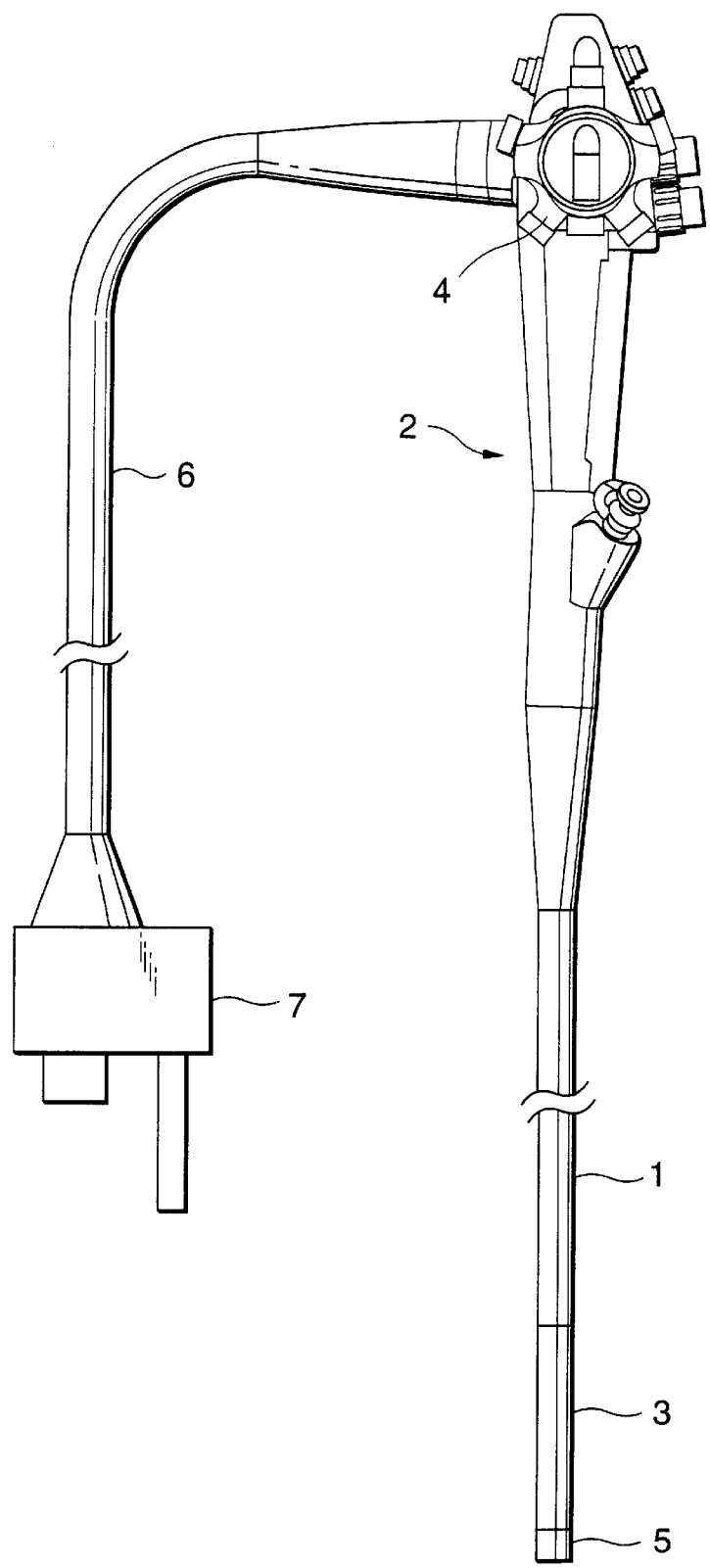
FIG. 4 is the exterior view of the endoscopic flexible tube of the invention.

FIG. 4 shows the general construction of an endoscope; its insertion portion to be inserted into a body cavity is sheathed with a flexible tube 1 the basal end of which is coupled to the lower end of a manipulating section 2.

Coupled to the distal end of the flexible tube 1 is a bendable portion 3 that is remotely manipulated by a control knob 4 in the manipulating section 2 so that it bends by a desired angle in a desired direction. Connected to the tip of the bendable portion 3 is a tip assembly 5 having built-in objective optics and other necessary components.

A flexible coupling tube 6 is coupled to the neighborhood of the upper end of the manipulating section 2 and a connector 7 to be connected to a video processor/light source unit (not shown) is provided at the distal end of the coupling tube 6.

Figure 5:
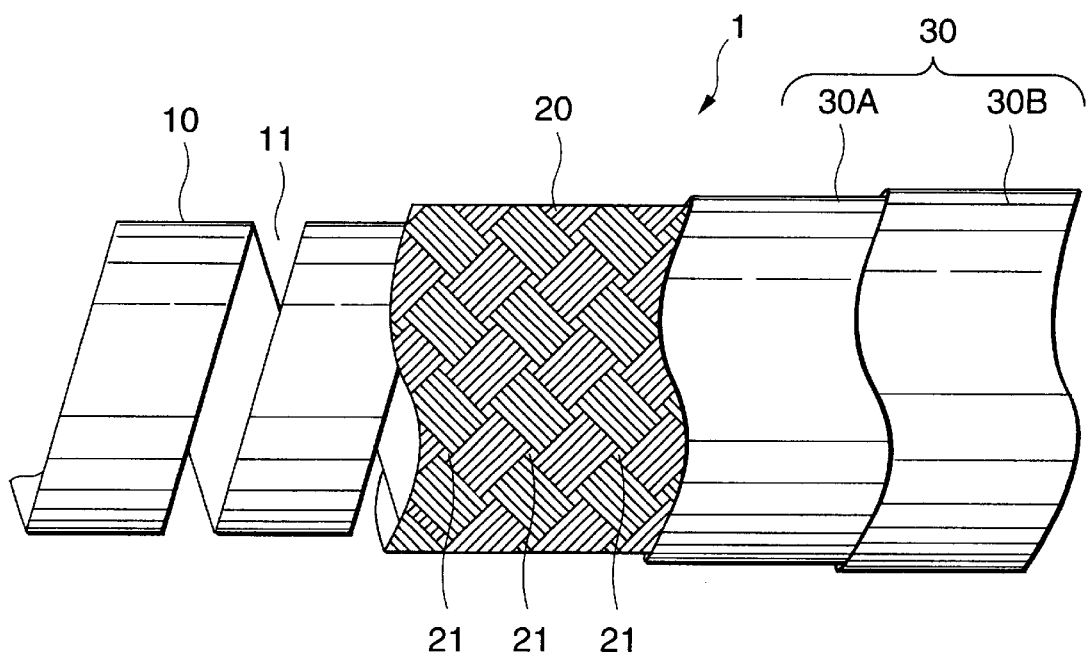
FIG. 5 is a side view of the endoscopic flexible tube of the invention, with its components being stripped away layer by layer.

FIG. 5 shows the structure of the flexible tube 1 around the insertion portion of the endoscope, with its components being stripped away layer by layer. The innermost layer comprises a helical tube 10 formed of a strip, typically made of stainless steel or copper alloy, that is wound in turns of a coil as spaced by gaps 11 in the pitch direction. In FIG. 5, the helical tube 10 consists of a single layer of windings but it may consist of windings turned in opposite directions to form two, three or more layers.

The outer surface of the helical tube 10 is covered with a reticulate tube 20 which is formed of reticulately braided bundles of metallic or non-metallic wires and which in turn is covered with a flexible jacket 30 on its outer surface. Indicated by 21 are mesh openings distributed uniformly in the reticulate tube 20.

In the embodiment under consideration, the jacket 30 has a dual structure consisting of the inner layer 30A and the outer layer 30B that have different characteristics and which are placed one on the other. Such characteristics are mechanical in nature (i.e., they affect the mechanics, or motion of the materials forming the layers 30A, 30B) and include slipping ability (i.e., lubricity) in the longitudinal direction. For example, the insertion (i.e., distal) side of the flexible tube 1 may have a layer 30A and/or 30B of a material having a higher lubricity than the material at a proximal side of the layer. Such an arrangement facilitates the insertion of the tube 1 into the body due to the low frictional resistance, while at the same time ensuring the user's grip on the tube to more easily push the tube into a patient's body. Another such characteristic includes flexibility, but additional mechanical characteristics may be readily appreciable by those skilled in the art. To make the jacket 30, pellets of the constituent materials are charged into an extrusion molding machine, heated to melt and cover the outer surface of the reticulate tube 20 directly and thereafter cooled as such into a tubular form.

Figure 1:
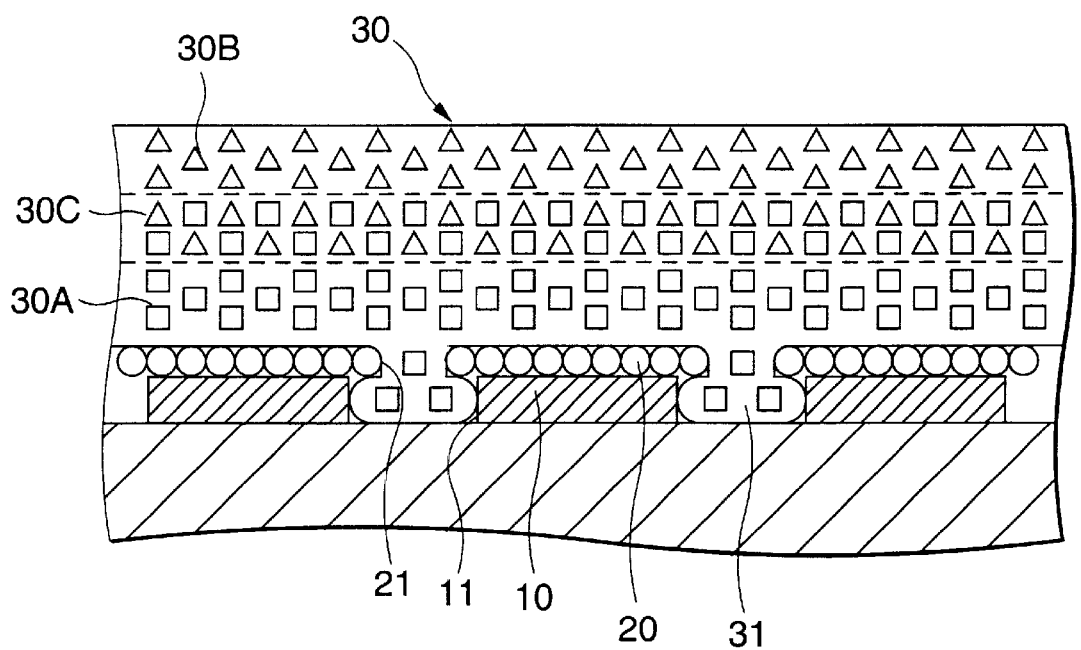
FIG. 1 is a partial enlarged longitudinal section of the jacket of an endoscopic flexible tube according to a first embodiment of the invention.

FIG. 1 is an enlarged partial section of the jacket 30. As shown, the extruded and molten constituent material of the inner layer 30A passes through the mesh openings 21 in the reticulate tube 20 to project inwardly through the gaps 11 formed in the helical tube 11 in the pitch direction. The molten constituent material in the gaps cools to solidify as such to form protrusions, one of which is indicated by 31 in FIG. 1.

Between the inner layer 30A and the outer layer 30B there is provided an area 30C that comprises a mixture of the constituent materials of the two layers which were mixed in a melten state and then cooled to solidify. The inner layer 30A and the outer layer 30B are integrally combined via the area 30C. For clarity, sections of the inner layer 30A and the outer layer 30B are indicated by □ and Δ, respectively, and the mixed area 30C by both □ and Δ.

The constituent material of the inner layer 30A should be a soft material that smoothly gets into the mesh openings 21 in the reticulate tube 20 to have good adhesion and which may be exemplified by a polyurethane group thermoplastic elastomer such as a polyurethane. The constituent material of the outer layer 30B should be harder than that of the inner layer 30A and have high chemical resistance and examples of such material are polyolefin group resin such as polyolefin and a polyamide group resin such as polyamide. Such materials are resistant to certain chemicals including disinfectants such as those of the hydrogen peroxide group and peroxyacetic acid group.

Figure 2:
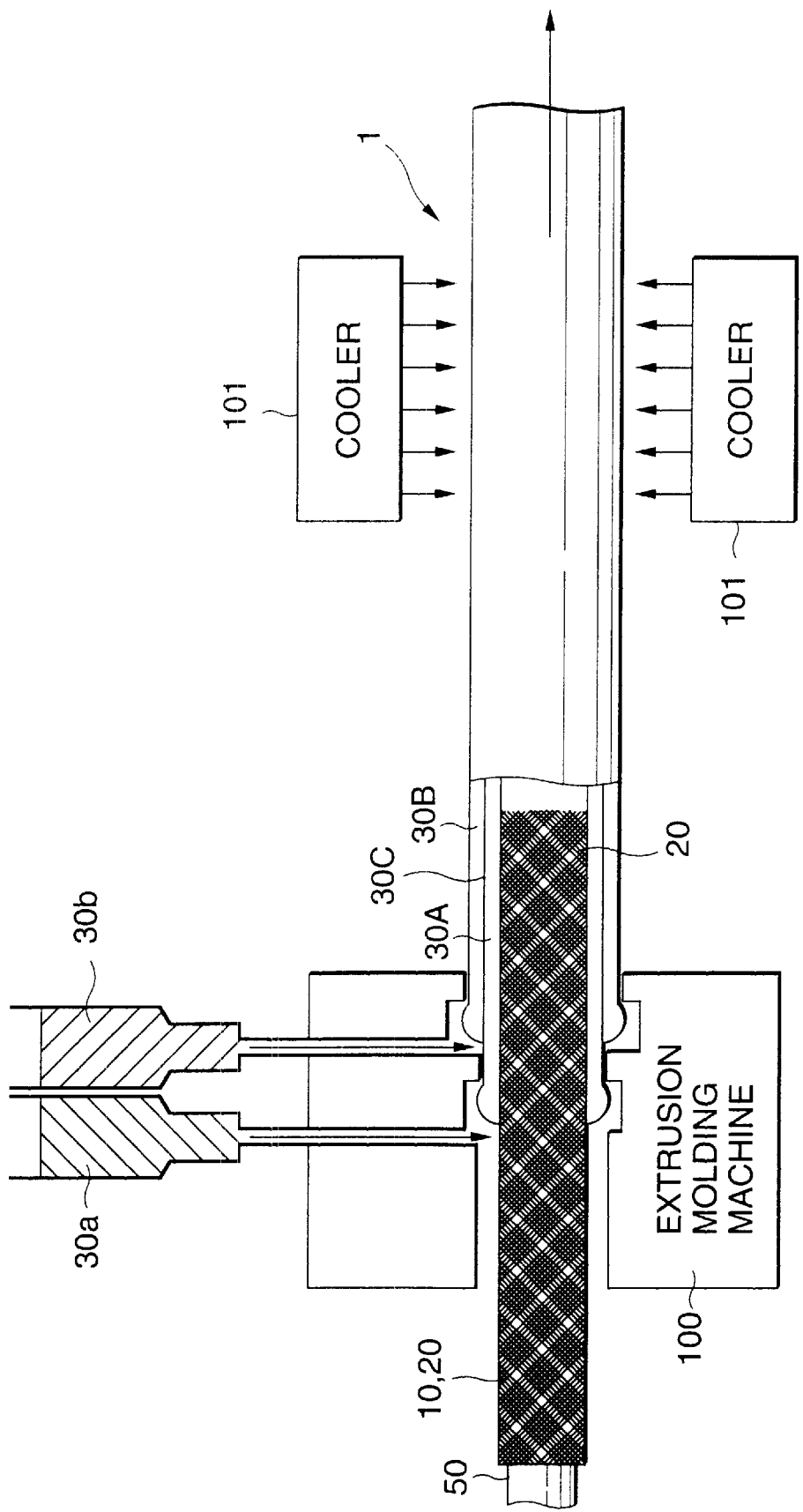
FIG. 2 is a sketch showing in longitudinal section how the endoscopic flexible tube according to the first embodiment of the invention can be fabricated.

FIG. 2 illustrates how the flexible tube 1 according to the embodiment under consideration can be fabricated with an extrusion molding machine 100. The helical tube 10 covered with the reticulate tube 20 is in turn coated with the constituent material 30a of the inner layer 30A and the constituent material 30b of the outer layer 30B as they are in a molten state. Indicated by 50 is a mandrel for supporting the helical tube 10 and the reticulate tube 20 while the inner and outer layers 30A and 30B are being formed.

Figure 3:
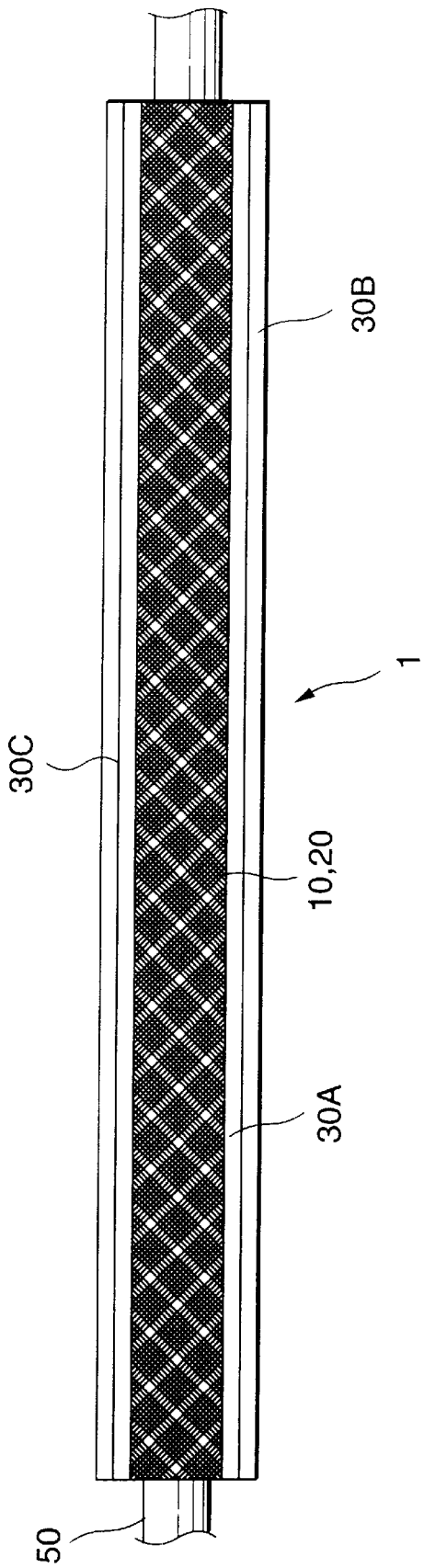
FIG. 3 is a longitudinal section of the endoscopic flexible tube according to the first embodiment of the invention.

As a result, the molten constituent materials 30a and 30b mix together to form the area 30C at the interface between the inner layer 30A and the outer layer 30B; as the individual components pass through a cooler 101, they solidify as such to produce the flexible tube 1 which is entirely shown in FIG. 3. The mandrel 50 has been removed from the tube.

Figure 6:
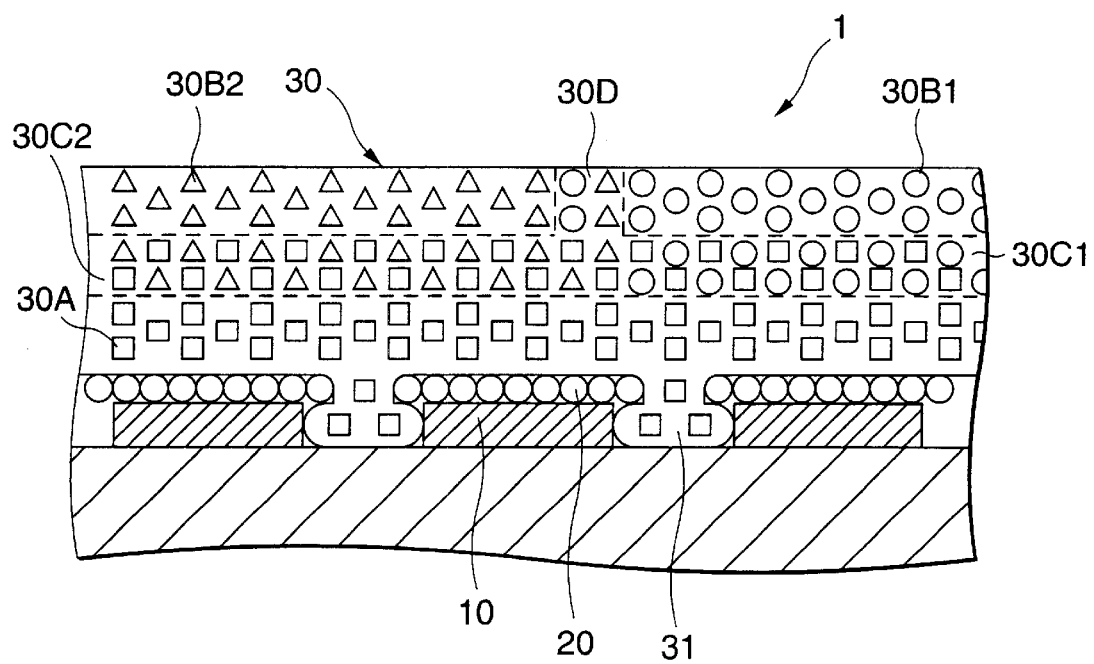
FIG. 6 is a partial enlarged longitudinal section of the jacket of an endoscopic flexible tube according to a second embodiment of the invention.

FIG. 6 is an enlarged partial section of the jacket 30 on the flexible tube 1 according to a second embodiment of the invention in which the outer layer 30B of the jacket comprises two portions with different degrees of hardness (soft portion 30B1 and hard portion 30B2) that extent along the longitudinal axis of the tube.

Between the soft portion 30B1 and the inner layer 30A, there is provided an area 30C1 which comprises a mixture of the constituent materials of 30B1 and 30A and via which the soft portion 30B1 of the outer layer 30B is integrally combined with the inner layer 30A. Between the hard portion 30B2 and the inner layer 30A, there is provided an area 30C2 which comprises a mixture of the constituent materials of 30B2 and 30A and via which the hard portion 30B2 of the outer layer 30B is integrally combined with the inner layer 30A.

At the boundary between the portions 30B1 and 30B2 of the outer layer 30B, there is provided an area 30D which comprises a mixture of the constituent materials of 30B1 and 30B2 that were mixed in a molten state and then cooled to solidify. The soft portion 30B1 and the hard portion 30B2 are integrally combined via the area 30D.

For clarity, sections of the inner layer 30A and the soft and hard portions 30B1 and 30B2 of the outer layer 30B are indicated by □, ○ and Δ, respectively; on the other hand, sections of mixed areas 30C1, 30C2 and 30D are indicated by ○+□, Δ+□ and ○+Δ, respectively.

The inner layer 30A and the portions 30B1 and 30B2 of the outer layer 30B are typically made of the same constituent materials as in the first embodiment. If desired, both the inner and outer layers may be made of similar materials having different degrees of hardness.

FIG. 7 illustrates how the flexible tube 1 according to the second embodiment can be fabricated with an extrusion molding machine 100. The constituent material 30b1 of the soft portion 30B1 of the outer layer 30B and the constituent material 30b2 of the hard portion 30B2 are selectively directed to a feed channel after switching with a valve 102. The second embodiment is identical to the first embodiment in the other aspects.

As a result, the molten constituent material 30a mixes with the molten constituent materials 30b1 and 30b2 to form the mixed areas 30C1 and 30C2 at the interface between the inner layer 30A and each of the soft and hard portions of the outer layer 30B while forming the mixed area 30D at the boundary between the soft and hard portions of the outer layer 30B. As the individual components pass through a cooler 101, they cool to solidify as such to produce the flexible tube 1 which is shown entirely in FIG. 8.

The thus fabricated flexible tube 1 according to the second embodiment of the invention is hard at the basal end but sufficiently soft at the distal end that it can be smoothly inserted into a body cavity. In addition, the jacket of the tube is highly durable and its overlapping layers will not separate during use.

The hardness of the outer layer 30B may vary in three or more portions along the longitudinal axis of the flexible tube. If desired, characteristics other than hardness may be varied to produce corresponding changes along the longitudinal axis of the tube.

The present invention is by no means limited to the two embodiments described above and its concept may be applied to either the flexible tube 1 or the flexible coupling tube 6. If desired, the inner layer 30A rather than the outer layer 30B of the jacket 30 may comprise a plurality of portions having different characteristics.

What is claimed is:

1. An endoscopic flexible tube comprising a helical tube formed of a strip wound in turns of a coil that are spaced by gaps in the pitch direction, a reticulate tube that is covered on the surface of said helical tube and which is formed of reticulately braided bundles of wires, and a flexible jacket that is coated on the outer surface of said reticulate tube and at least part of which has a multi-layered structure comprising a plurality of superposed layers, wherein:

two overlapping layers in the multi-layered structure portion of said jacket are configured to be integrally combined via an extrusion molding process at an area that comprises a mixture of constituent materials of each of said two layers; and an inner layer of said two overlapping layers of said multi-layered structure portion of said jacket protrudes inwardly through mesh openings of said reticulate tube and into a said gap of said coil.

2. The endoscopic flexible tube according to claim 1, wherein said inner layer of the multi-layered structure portion of said jacket is made of a synthetic resin material and an outer layer is made of synthetic resin material that is harder than said synthetic resin material of said inner layer, the outer layer material being resistant to disinfectants.

3. The endoscopic flexible tube according to claim 2, wherein the disinfectants are at least one of a hydrogen peroxide group and a peroxyacetic acid group.

4. The endoscopic flexible tube according to claim 1, wherein at least one of said inner layer and said outer layer of the multi-layered structure portion of said jacket have a plurality of adjacent portions with different mechanical characteristics along a longitudinal axis of said endoscopic flexible tube and wherein adjacent ones of said portions are integrally combined via an area that comprises a mixture of the constituent materials of each of said two adjacent portions.

5. The endoscopic flexible tube according to claim 4, wherein the mechanical characteristics are at least one of lubricity and flexibility.

6. The endoscopic flexible tube according to claim 1, wherein the mixture area in the multi-layered structure portion of said jacket is formed of the constituent materials on the opposite sides that intermingle when said constituent materials are molten simultaneously.

* * * * *